US008398655B2

(12) United States Patent
Cheng et al.

(10) Patent No.: US 8,398,655 B2
(45) Date of Patent: Mar. 19, 2013

(54) INTEGRATED DOUBLE CLIPS APPLIER WITH DIVISION DEVICE FOR CLAMPING CLIPS

(75) Inventors: Ming-Huei Cheng, Taipei (TW); Steve L. Henry, Taipei (TW)

(73) Assignees: Ming-Huei Cheng, Taipei (TW); Steve L. Henry, Taipei (TW); Holger Engel, Taipei (TW)

( * ) Notice: Subject to any disclaimer, the term of this patent is extended or adjusted under 35 U.S.C. 154(b) by 259 days.

(21) Appl. No.: 12/801,412

(22) Filed: Jun. 8, 2010

(65) Prior Publication Data
US 2010/0318103 A1 Dec. 16, 2010

(30) Foreign Application Priority Data
Jun. 15, 2009 (TW) .............................. 98119899 A (51) Int. Cl.
*A61B 17/10* (2006.01)
(52) U.S. Cl. .................................................... 606/142
(58) Field of Classification Search ................. 606/139, 606/142, 143, 205; 227/19, 175.1, 901
See application file for complete search history.

(56) References Cited

U.S. PATENT DOCUMENTS
3,873,016 A * 3/1975 Fishbein ......................... 227/83
* cited by examiner

*Primary Examiner* — Ryan Severson
*Assistant Examiner* — Jonathan W Miles
(74) *Attorney, Agent, or Firm* — Bacon & Thomas, PLLC (57) ABSTRACT

The present invention relates to a clip applier for clipping and dividing blood vessels, including: a handle; a first jaw unit; and a second jaw unit. The clip applier of the present invention can bring up two ligating clips at the same time with the first jaw unit and the second jaw unit, whereas the two clamping positions of the blood vessel can be clamped with the ligating clips simultaneously by the clip applier of the present invention in a single step, and thus the operating steps can be simplified, and the time involved with the surgical operation can be shortened.

20 Claims, 14 Drawing Sheets

INTEGRATED DOUBLE CLIPS APPLIER WITH DIVISION DEVICE FOR CLAMPING CLIPS

BACKGROUND OF THE INVENTION

1. Field of the Invention

The present invention relates to a clip applier and, more particularly, to a clip applier for clamping one or more ligating clips simultaneously.

2. Description of Related Art

During a surgical operation, a temporary ligating of the blood vessels is usually applied to prevent bleeding of blood vessels, and some tools for such operations have been developed to assist the ligation of the blood vessels. Commonly, for example, a clip applier is used first to pick up a ligating clip, and then blood vessels are ligated by the ligating clip upon the ligating clip being clipped/deformed by the clip applier.

Figure 1:
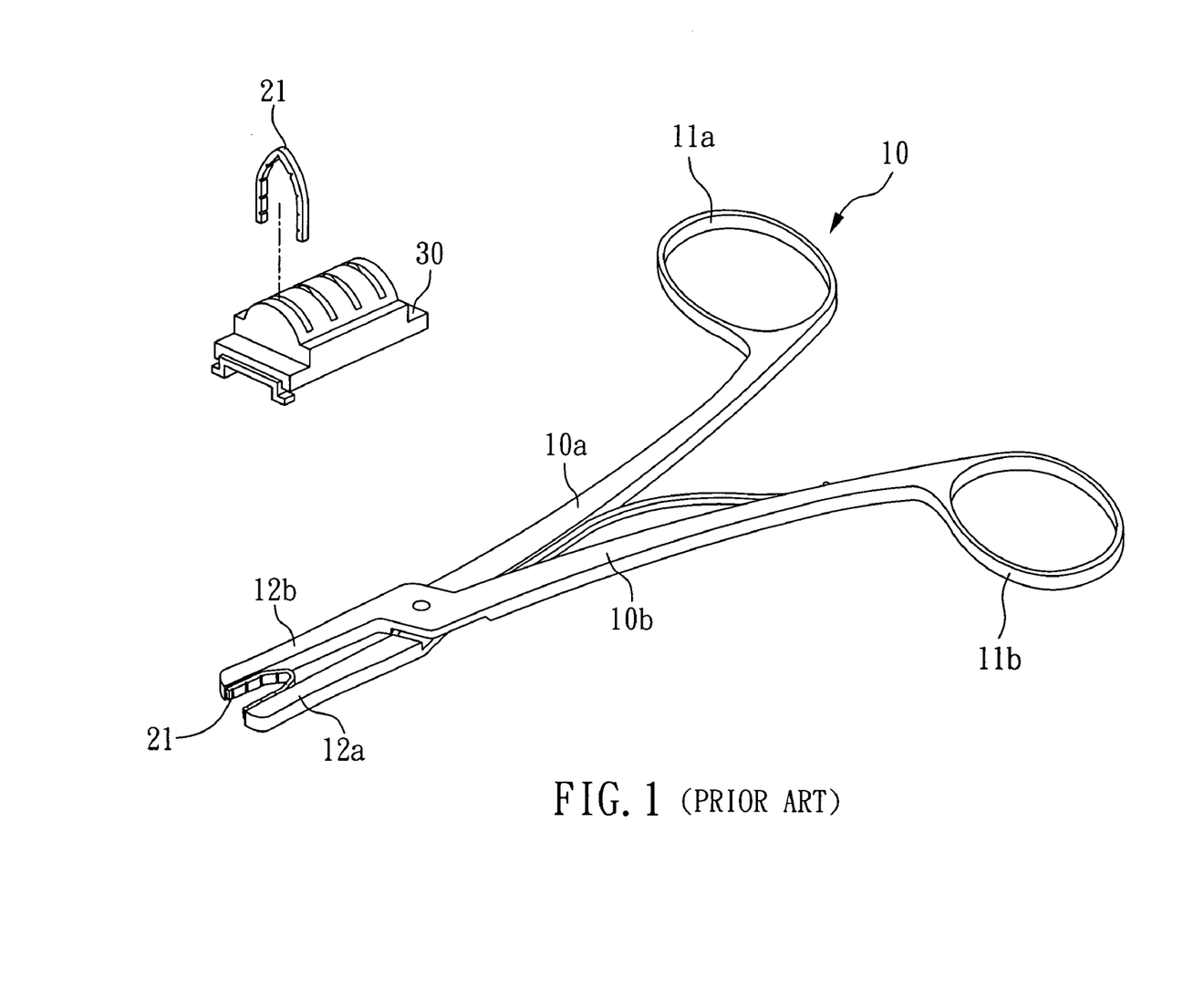
FIG. 1 is a schematic view of a traditional clip applier for clamping ligating clips.

Reference with FIG. 1, a conventional clip applier 10 for clamping ligating clips is shown, which comprises: a first clip unit 10a having a first handle 11a at one end and a first jaw unit 12a at another end; and a second clip unit 10b having a second handle lib at one end and a second jaw unit 12b at another end. Hence, the ligating clip 21 packed on the clip cartridge 30 can be brought up from the clip cartridge 30 by the first jaw unit 12a and the second jaw unit 12b of the clip applier 10.

Though the clip applier described above is advantageous in its simple structure and is easily manufactured, when applied to the surgical operations, the clip applier described above cannot be easily handled. In detail, when using the clip applier for clipping blood vessels, two ends of the blood vessel should be clipped sequently by using the clip applier with the ligating clips (in which the ligating clips should be brought up from the clip cartridge and then two positions arranged at the two sides of the cutting position of the blood vessel are clipped with those ligating clips). Then, a cutting tool such as a surgical blade is used to cut the blood vessel at the appropriate location. However, considering the above method, a lengthy operating time is involved due to the complex steps for the clipping and cutting of the blood vessels, which is restricted with those inconvenient tools.

SUMMARY OF THE INVENTION

An object of the present invention is to provide a clip applier for clamping ligating clips, which can bring up two ligating clips at the same time and clamp the two clamping positions of the blood vessel with the ligating clips simultaneously in a single step, and thus the operating steps can be simplified, and the time involved with the surgical operation can be shortened.

In order to obtain the above object, the present invention provides a clip applier for clamping ligating clips, including: a handle unit; a first jaw unit including a first end having a first upper clipping portion and a first lower clipping portion, there being a first interval between the first upper clipping portion and the first lower clipping portion; and a second jaw unit including a second end having a second upper clipping portion and a second lower clipping portion, there being a second interval between the second upper clipping portion and the second lower clipping portion, wherein the first upper clipping portion corresponds to the second upper clipping portion so as to clamp a first ligating clip by operating the handle unit, and the first lower clipping portion corresponds to the second lower clipping portion so as to clamp a second ligating clip by operating the handle unit.

Therefore, one or more ligating clips can be clamped simultaneously at a single step because the first jaw unit and the second jaw unit of the clip applier of the present invention independently has one or more clipping portions (i.e. the first jaw unit has a first upper clipping portion and a first lower clipping portion, the second jaw unit has a second upper clipping portion and a second lower clipping portion). Correspondingly, two clamping positions beside the cutting position of the blood vessel can be clamped with the ligating clips simultaneously at a single step.

Preferably, the clip applier for clamping ligating clips of the present invention may further comprise a cutting unit and an advancing unit, wherein the cutting unit connects to the advancing unit and the cutting unit is moved by the operation of the advancing unit, one end of the cutting unit locates between the first jaw unit and the second jaw unit, and the advancing unit enables the cutting unit to move toward the ends of the first jaw unit and the second jaw unit. Herein, the structure of the advancing unit is not specially limited, as long as it can be moved enabling the cutting unit to be moved toward the ends of the first jaw unit and the second jaw unit.

After the two clamping positions have been clamped, the advancing unit is moved and enables the cutting unit to move toward the cutting position of the blood vessel to cut the blood vessel at the cutting position. Therefore, an extra step of taking the cutting unit can be eliminated, the cutting steps at the surgical operation can be simplified, and the operation time can be shortened.

According to the present invention, the cutting unit may preferably comprise a first cutting component and a first connecting component, wherein the first cutting component connects with the first connecting component, and the first connecting component connects with the advancing unit. The cutting component may preferably be a blade or a billhook.

According to the present invention, the cutting unit may preferably further comprise a second cutting component and a second connecting component, the second cutting component connects with the second connecting component, and the first connecting component and the second connecting component are pivotally connected.

According to the present invention, the cutting unit further comprises a second flexible element locating between the first connecting component and the second connecting component. Hence, after an applied strength ceases, the second flexible element may provide a returning force enabling the first connecting component and the second connecting component to return to its original position (before the application of the strength). The second flexible element is not specially limited, as long as it can provide a returning force. For example, the second flexible element may be a spring or a leaf spring.

According to the present invention, the handle unit may have a first handle and a second handle, the first jaw unit and the first handle may integrally form a first clip unit, the second jaw unit and the second handle may integrally form a second clip unit, and the first clip unit and the second clip unit may be pivotally connected. Herein, the first clip unit or the second clip unit may have a groove for receiving the advancing unit and enabling the advancing unit to move in the groove; or the clip applier may further comprise a fixing part locating on the first clip unit or on the second clip unit, wherein the fixing part has a channel cavity, and the advancing unit passes through the channel cavity to enable the advancing unit to move therein and ensures the advancing unit moves linearly.

According to the present invention, the clip applier for clamping ligating clips may further comprise an elastic element received in the groove, wherein the two ends of the elastic element connect with the advancing unit and the edge of the groove respectively; or the elastic element may wrap around the advancing unit, and two ends of the elastic element connect with the advancing unit and the fixing part respectively. Therefore, after an applied strength ceases, the elastic element may provide a returning force enabling the advancing unit to return to its original position (i.e., before the application of the strength).

According to the present invention, the clip applier for clamping ligating clips may further comprise a first flexible element locating between the first clip unit and the second clip unit. Therefore, after an applied strength ceases, the first flexible element may provide a returning force enabling the first clip unit and the second clip unit to return to its original position (i.e., before the application of the clamping force). Herein, the first flexible element is not specially limited, as long as it can provide a returning force, for example, the first flexible element may be a spring or a leaf spring.

According to the present invention, the first jaw unit may further comprise a first elongation part, the second jaw unit may further comprise a second elongation part, the first elongation part connects to the first end, and the second elongation part connects to the second end. The first elongation part connects to the first end with a first angle, and the second elongation part connects to the second end with a second angle, in which, the first angle and the second angle may independently be 90 to 180 degrees. Preferably, the first angle and the second angle are the same. Therefore, the first jaw unit and the second jaw unit may be both formed in a straight shape or an angled shape as needed. When a blood vessel locates in a deeper position during the surgical operation, the first jaw unit and the second jaw unit with an angled shape may be selectively used for clamping the vessel. Therefore, during the clamping step, the blood vessel can be easily clamped and cut with the end extended from the first elongation part of the jaw unit having an angled shape.

As mentioned above, the clip applier for clamping ligating clips of the present invention can bring up two ligating clips at the same time and clip the two clamping positions of the blood vessel with the ligating clips simultaneously in a single step, and thus the operating steps can be simplified, and the time involved can be shortened. Besides, the clip applier of the present invention further comprises a cutting unit that can move toward the cutting position of the blood vessel along with the advancing unit to cut the blood vessel. Therefore, compared with the traditional clip applier without a cutting unit, the clip applier of the present invention may enable a step of taking the cutting unit to be eliminated, thereby enabling the cutting steps at the surgery operation to be simplified, and enabling the operation time to be shortened.

DETAILED DESCRIPTION OF THE PREFERRED EMBODIMENT

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety.

Example 1

Figure 2A:
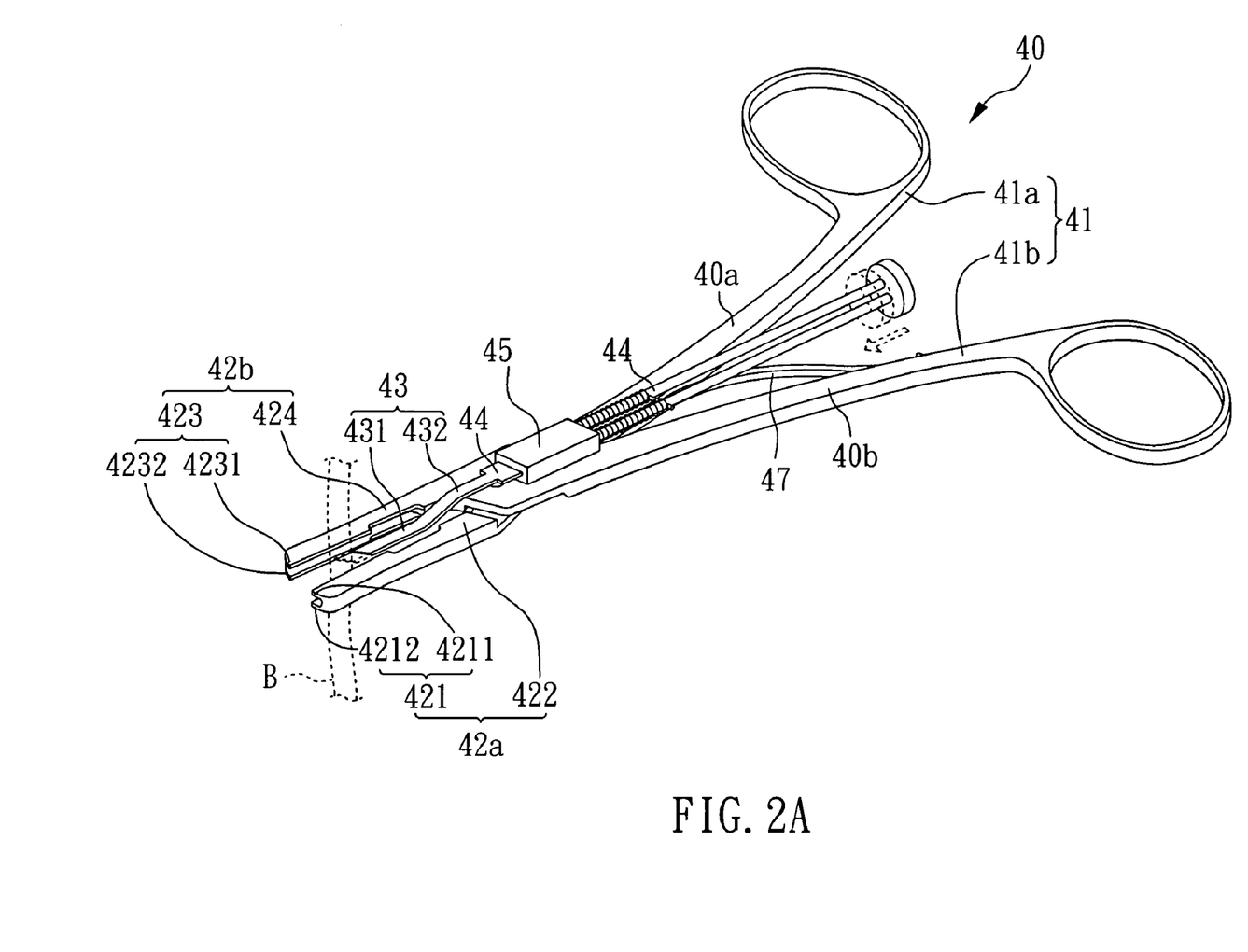
FIG. 2A is a schematic view of a clip applier for clamping ligating clips of a preferred example of the present invention.

With reference to FIG. 2A, there is shown a clip applier 40 for clamping ligating clips, which comprises: a handle unit 41; a first jaw unit 42a including a first end 421 and a first elongation part 422, wherein the first end 421 has a first upper clipping portion 4211 and a first lower clipping portion 4212; a second jaw unit 42b including a second end 423 and a second elongation part 424, wherein the second end 423 has a second upper clipping portion 4231 and a second lower clipping portion 4232; a cutting unit 43 having a first cutting component 431 and a first connecting component 432, wherein the first cutting component 431 connects with the first connecting component 432; and an advancing unit 44 connecting with the first connecting component 432 of the cutting unit 43, whereby the cutting unit 43 can be moved by the advancing unit 44.

Herein, the first end 421 connects to the first elongation part 422 with an angle of 180°; and the second end 423 connects to the second elongation part 424 with an angle of 180°. Hence, the first jaw unit 42a and the second jaw unit 42b are both formed in a straight shape. In the present example, the cutting component 431 is a blade.

Referring with FIG. 2A, in the present example, the handle unit 41 has a first handle 41a and a second handle 41b, in which the first jaw unit 42a and the first handle 41a are integrally formed as a first clip unit 40a, the second jaw unit 42b and the second handle 41b are integrally formed as a second clip unit 40b, and the first clip unit 40a and the second clip unit 40b are pivotally connected. Herein, the first clip unit 40a and the second clip unit 40b are two elongated arms.

Figure 2B:
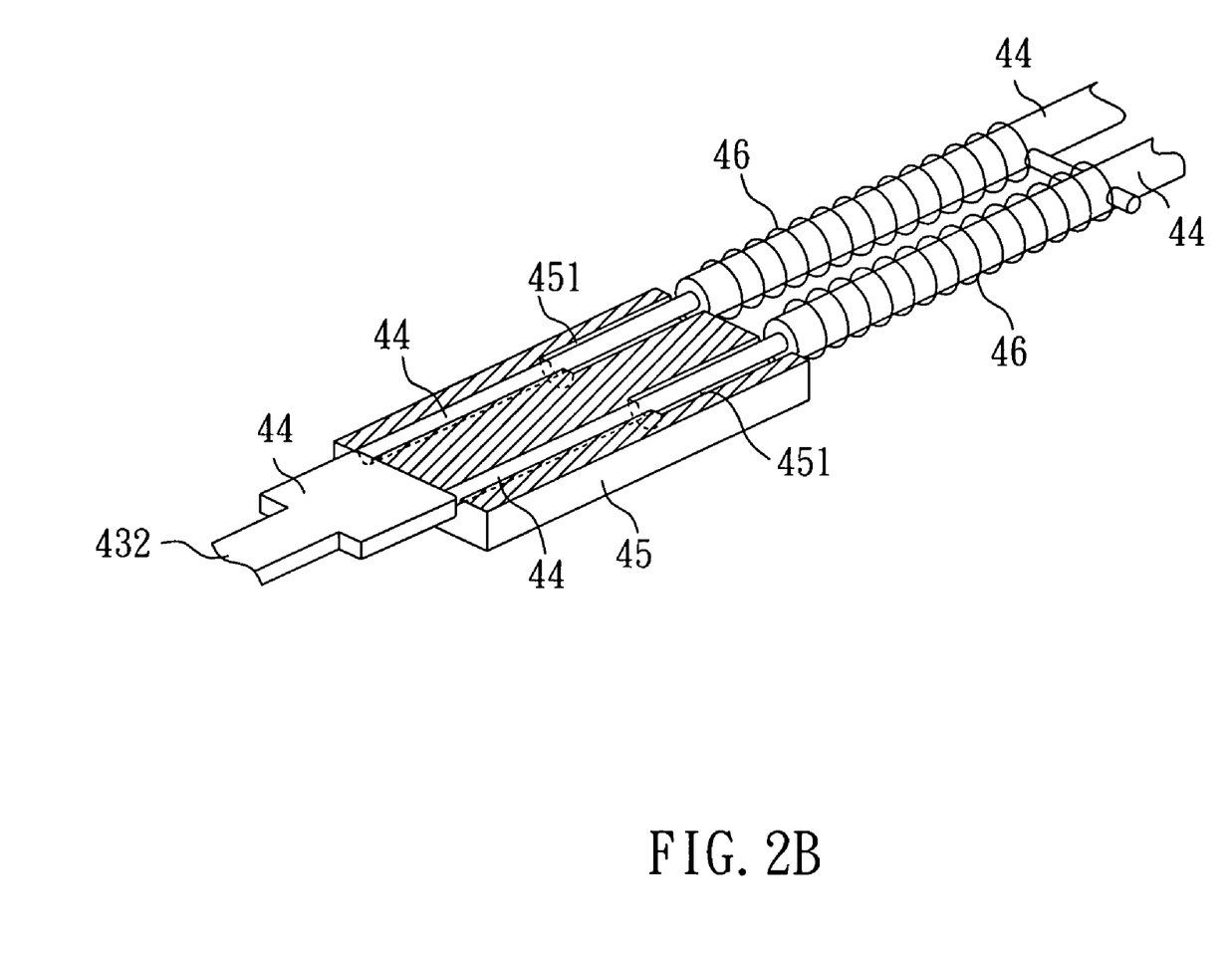
FIG. 2B is a schematic view showing the combination of the fixing part, the advancing unit, and the elastic element of the present invention.

Referring with FIG. 2A (also referring with FIG. 2B), the clip applier 40 of the present example comprises a fixing part 45 locating on the second clip unit 40b, wherein the fixing part 45 has a channel cavity 451 (as shown in FIG. 2B), and the advancing unit 44 passes through the channel cavity 451. Therefore, the channel cavity 451 enables the advancing unit 44 to move therein and ensures the advancing unit 44 moves linearly. As shown in FIG. 2A, the clip applier 40 also comprises an elastic element 46 wrapping around the advancing unit 44, wherein the two ends of the elastic element 46 connect with the advancing unit 44 and the fixing part 45 respectively. Therefore, after an applied strength ceases, the elastic element 46 may provide a returning force enabling the advancing unit 44 to return to its original position (i.e., before the application of the strength).

Besides, as shown in FIG. 2A, the clip applier 40 further comprises a first flexible element 47 locating between the first clip unit 40a and the second clip unit 40b to provide a returning force. Therefore, after an applied strength ceases, the first flexible element 47 may provide a returning force enabling the first clip unit 40a and the second clip unit 40b to each return to its original position (i.e., before the application of the clamping force). Herein, the first flexible element 47 is a leaf spring.

Figure 2C:
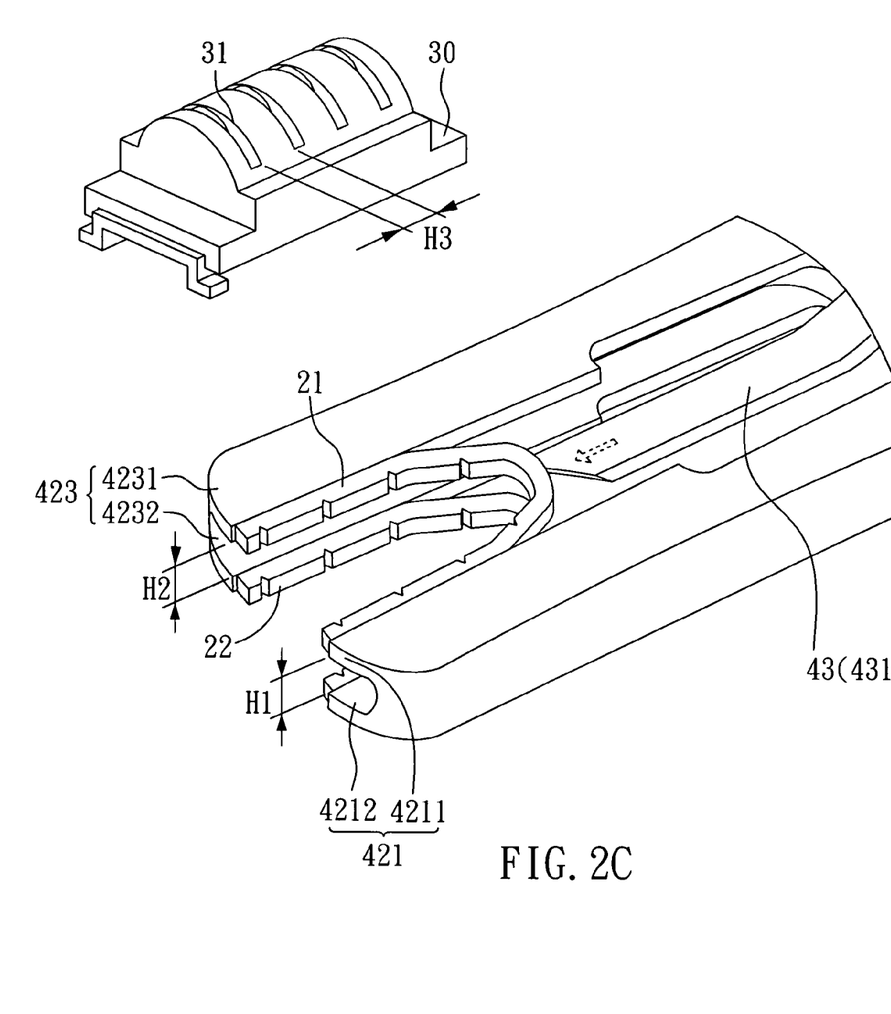
FIG. 2C is an enlarged schematic view showing the first jaw unit and the second jaw unit of the present invention.

Referring with FIG. 2C, an enlarged figure comprising the first jaw unit and the second jaw unit is shown. In detail, a first interval H1 exists between the first upper clipping portion 4211 and the first lower clipping portion 4212, a second interval H2 exists between the second upper clipping portion 4231 and the second lower clipping portion 4232, wherein the first upper clipping portion 4211 corresponds to the second upper clipping portion 4231 so as to clamp a first ligating clip 21 by operating the handle unit 41 (as shown in FIG. 2A), and the first lower clipping portion 4212 corresponds to the second lower clipping portion 4232 so as to clamp a second ligating clip 22 by operating the handle unit 41 (as shown in FIG. 2A). Referring with FIG. 2C, the first interval H1 and the second interval H2 correspond to the interval H3 between the slots 31 of the clip cartridge 30, which means the first interval H1 and the second interval H2 are generally the same as the interval H3. Therefore, the ligating clips 21,22 packed adjacently in the slots 31 can be clamped by the first end 421 of the first jaw unit 42a and the second end 423 of the second jaw unit 42b simultaneously. Also referring with FIGS. 2A and 2C, the advancing unit 44 enables one end of the cutting unit 43 (i.e. the first cutting component 431) to move between the first interval H1 and the second interval H2 and move toward the first end 421 of the first jaw unit 42a and the second end 423 of the second jaw unit 42b.

Figure 3A:
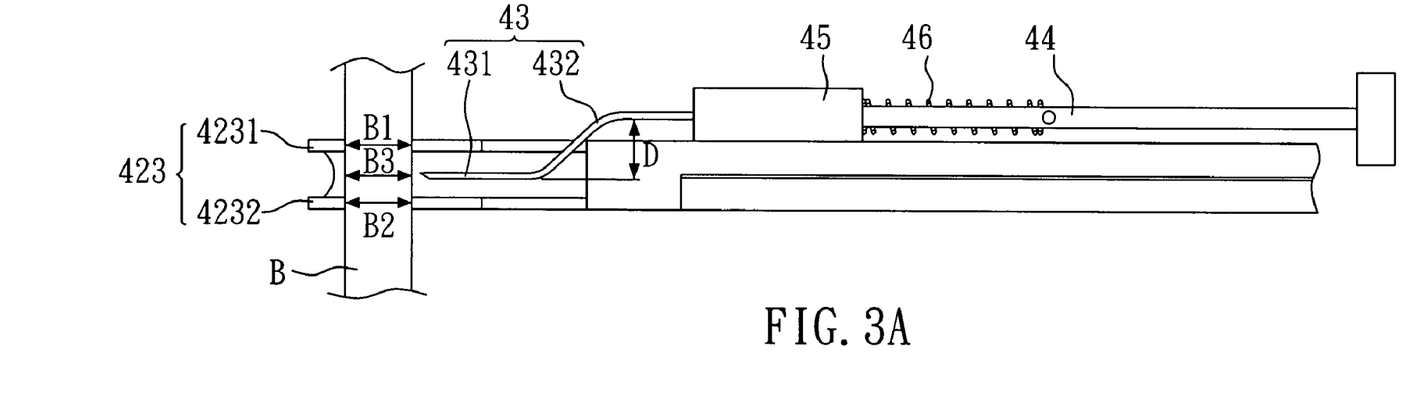
FIGS. 3A and 3B are schematic views showing the operations of the clip applier of a preferred example of the present invention.
Figure 3B:
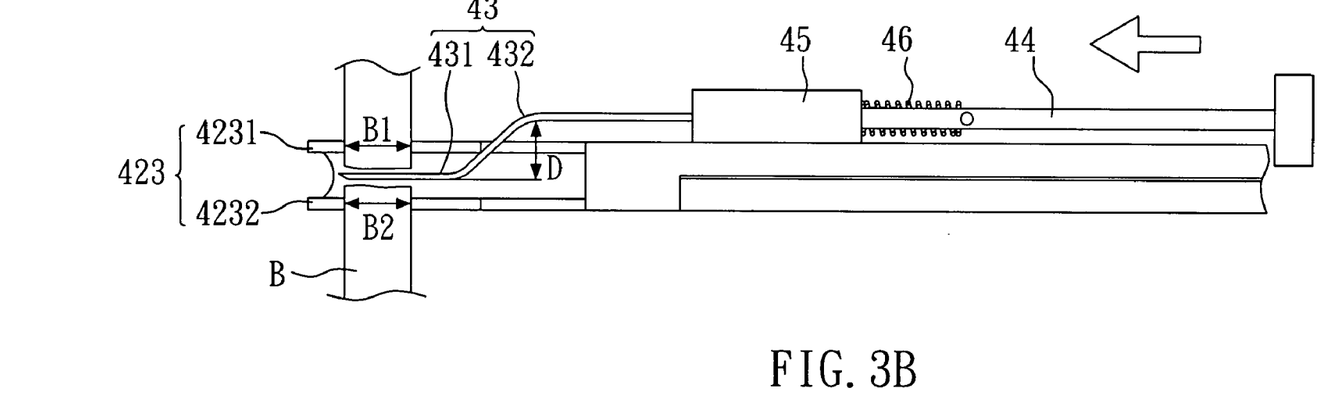
Figure 3C:
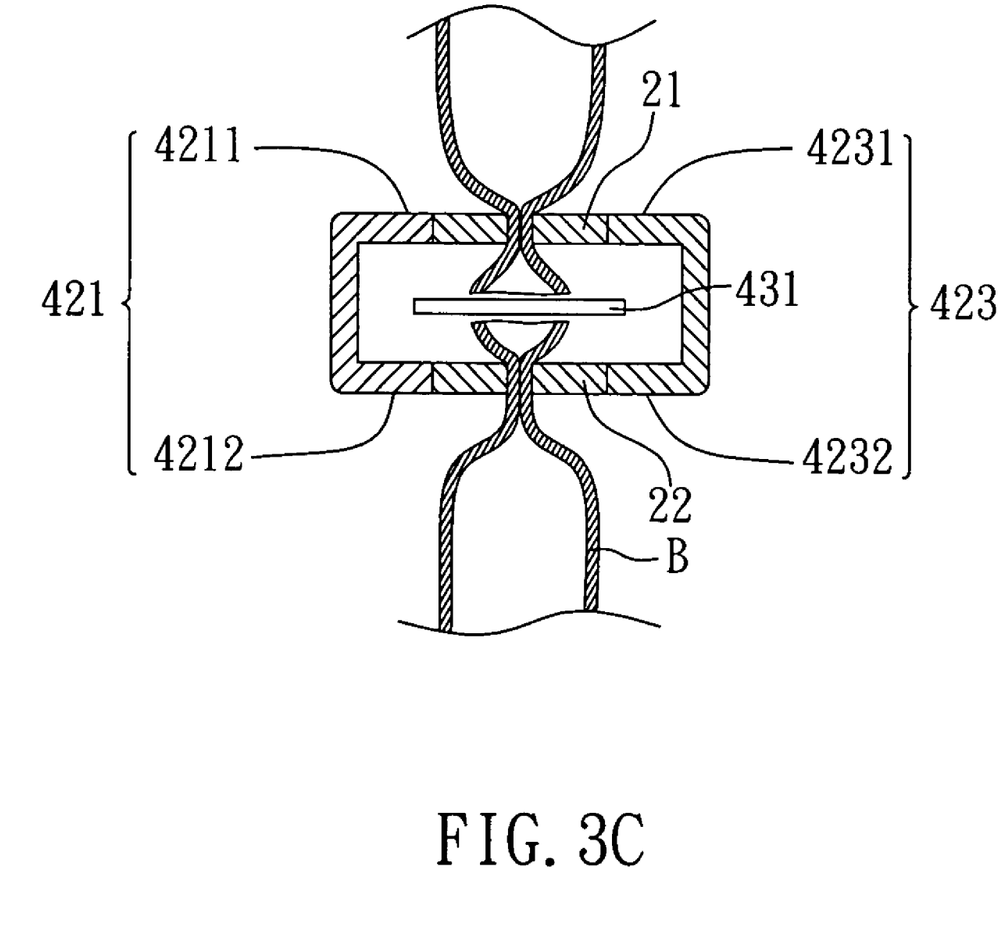
FIG. 3C is a schematic view showing a clamped blood vessel cut by the clip applier of the present invention.

Hence, referring with FIGS. 3A and 3B (also referring with FIG. 3C), when the clip applier is applied for cutting the blood vessel B at the cutting position B3, the processing steps are as follow: first, the first upper clipping portion 4211 and the second upper clipping portion 4231 together clamp a first ligating clip (not shown) for clamping the blood vessel B at the clamping position B1, and the first lower clipping portion 4212 and the second lower clipping portion 4232 together clamp a second ligating clip (not shown) for clamping the blood vessel B at the clamping position B2; and then, as shown in FIG. 3B (also reference with FIG. 3C), the advancing unit 44 is moved to compress the elastic element 46 and push the cutting unit 43 to move toward the blood vessel B, and therefore the blood vessel B is cut at the cutting position B3. Herein, since the cutting component 431 is set corresponding to the cutting position B3 locating between the clamping positions B1 and B2, the connecting component 432 has an angled portion to form a drop height D enabling the cutting component 431 to locate corresponding to the cutting position B3.

Example 2

Figure 4:
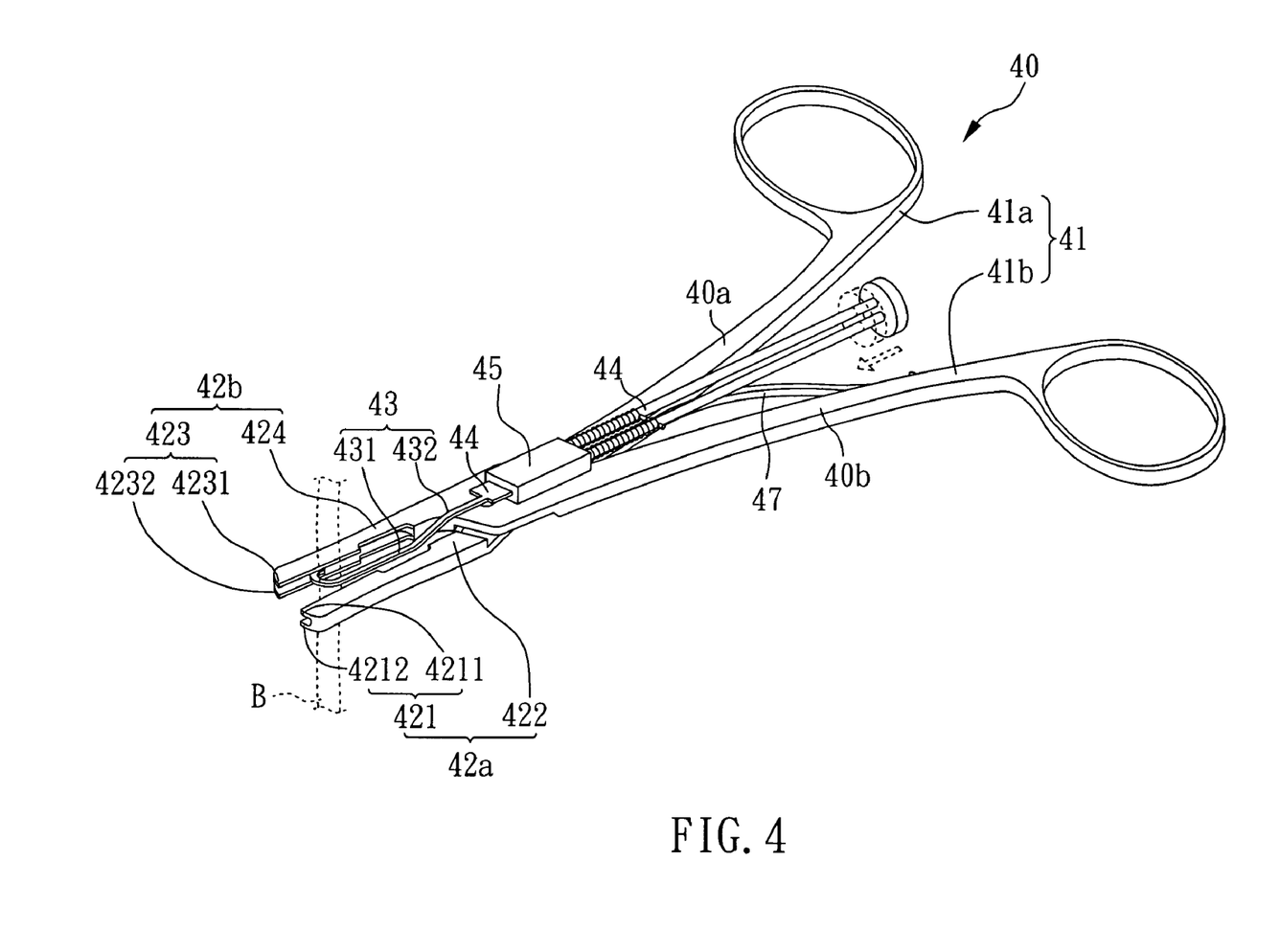
FIG. 4 is a schematic view of a clip applier for clamping ligating clips of another preferred example of the present invention.

Referring with FIG. 4, a clip applier 40 for clamping ligating clips of the present example is shown. Except that the cutting component 431 of the cutting unit 43 is a billhook in the present example, the other features and components are the same as those of example 1.

According to the present example, the clip applier 40 may be utilized in the same steps as shown in FIGS. 3A to 3B. The two clamping positions are clamped in a single step, and then the cutting unit is moved toward the cutting position to cut the blood vessel to complete the cutting process by using the clip applier 40 of the present example.

Referring with FIG. 4, when the cutting unit 43 moves with the advancing unit 44 toward the cutting position of the blood vessel, the blood vessel may not be cut at the first time due to the elasticity of the blood vessel, and then when the advancing unit 44 moves back to its original position after an applied strength ceases, the blood vessel is cut by the trenchant edge of the cutting component 431 (the billhook) of the cutting unit 43.

Example 3

Figure 5:
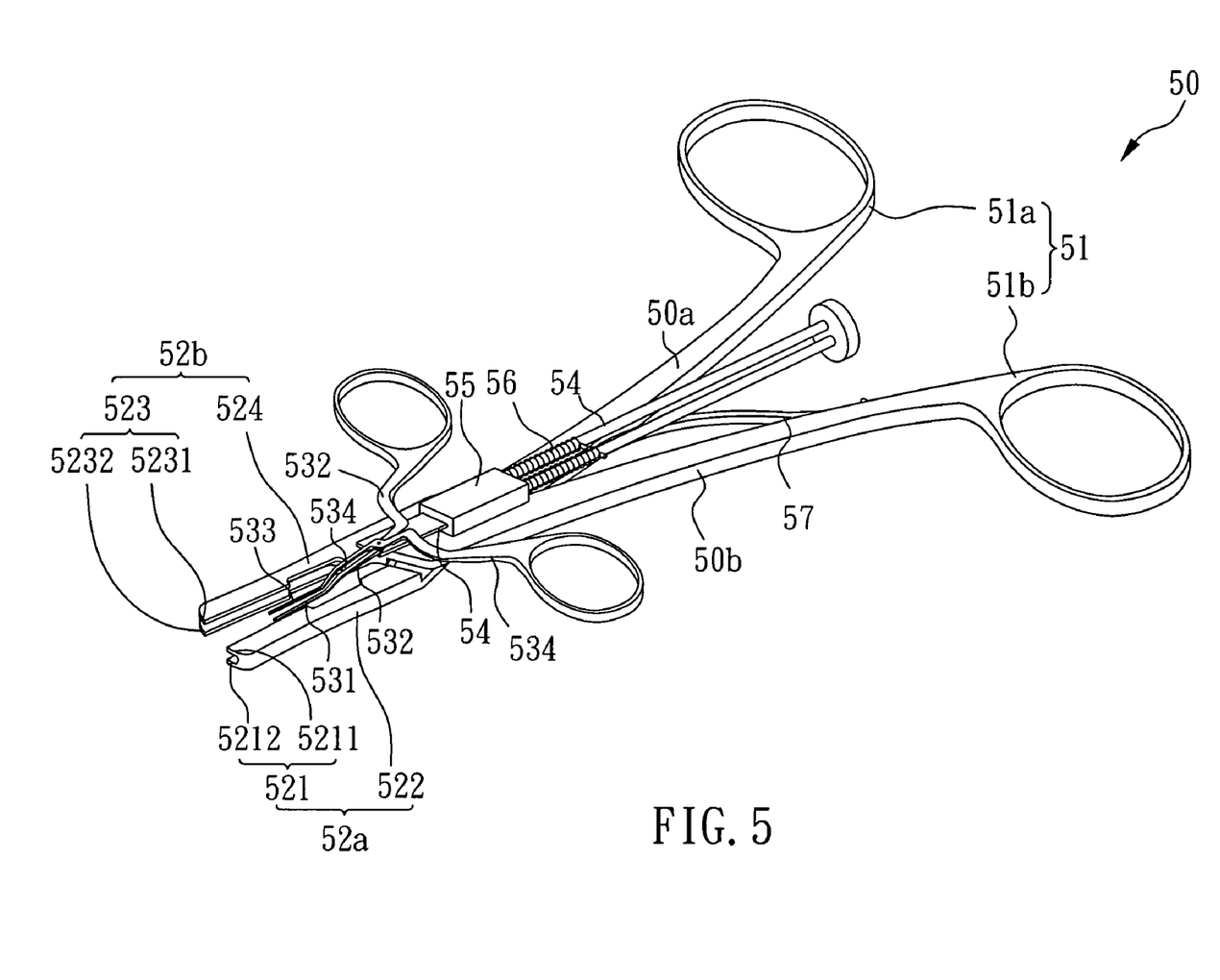
FIG. 5 is a schematic view of a clip applier for clamping ligating clips of still another preferred example of the present invention.

Referring with FIG. 5, a clip applier 50 for clamping ligating clips of the present example is shown. Except that the cutting unit 53 comprises a first cutting component 531, a first connecting component 532, a second cutting component 533, and a second connecting component 534; the first cutting component 531 connects to the first connecting component 532; the second cutting component 533 connects to the second connecting component 534; and the first connecting component 532 and the second connecting component 534 are pivotally connected in the present example, the other features and components are the same as those of example 1. Moreover, in the present example, the first cutting component 531 and the first connecting component 532 are integrally formed as an elongated arm, and also the second cutting component 533 and the second connecting component 534 are integrally formed as an elongated arm.

Therefore, the clip applier 50 of the present example may be utilized (operated) by the same steps shown in FIGS. 3A to 3B. The two clamping positions are clamped in a single step, and then the cutting unit is moved toward the cutting position to cut/scissor the blood vessel to complete the cutting process by using the clip applier of the present example.

Example 4

Figure 6A:
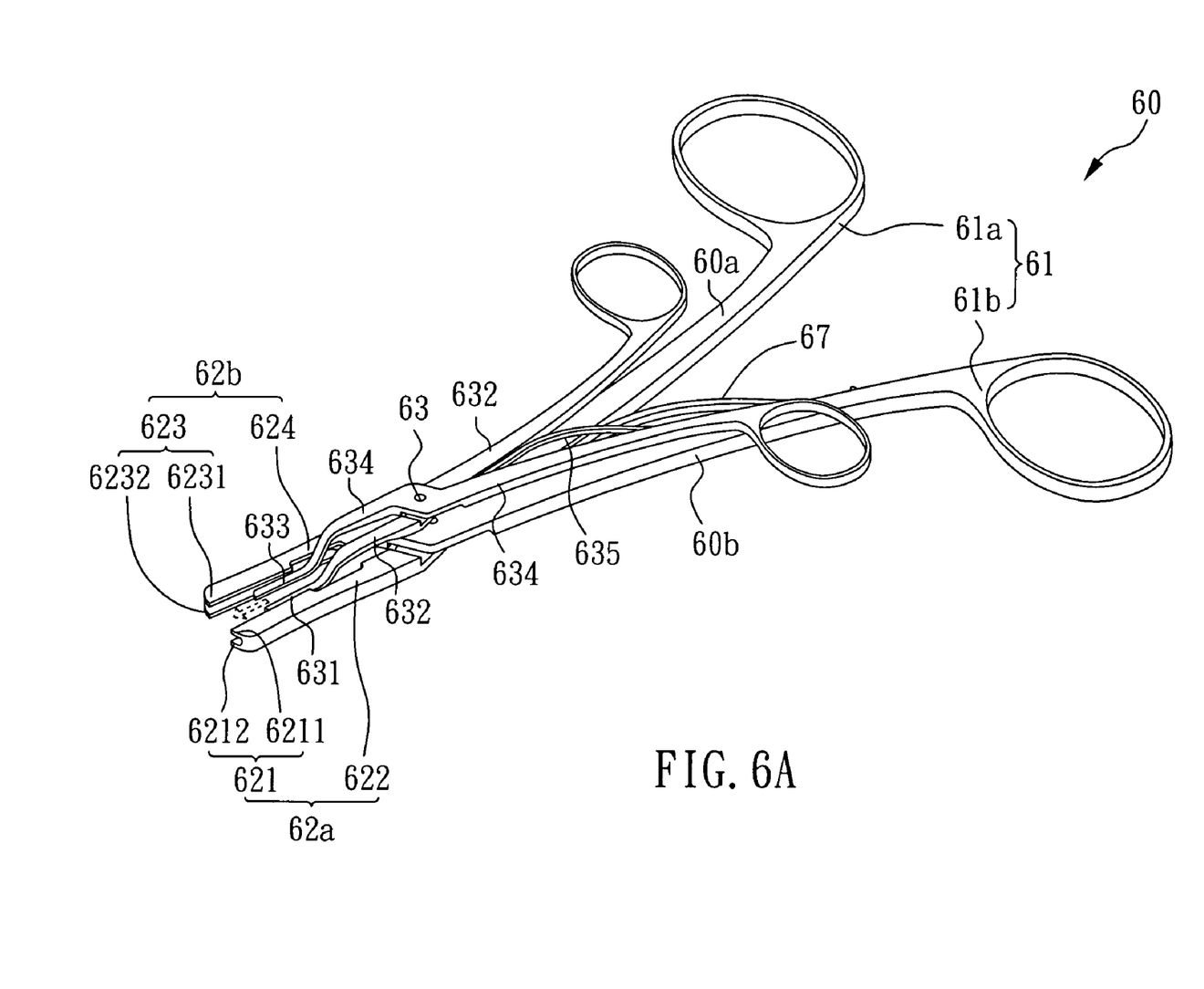
FIG. 6A is a schematic view of a clip applier for clamping ligating clips of still another preferred example of the present invention.

Referring with FIG. 6A, a clip applier 60 for clamping ligating clips of the present example is shown. Except that the cutting unit 63 of the present example further comprises a second flexible element 635, and the performing action of the clip applier 60 of the present example is different from that of examples 1 and 2, the other features and components in the present example are the same as those of example 3.

Referring with FIG. 6A, the cutting unit 63 of the clip applier 60 of the present example comprises a first cutting component 631, a first connecting component 632, a second cutting component 633, and a second connecting component 634, in which the first cutting component 631 connects with the first connecting component 632, the second cutting component 633 connects with the second connecting component 634, and the first connecting component 632 and the second connecting component 634 are pivotally connected. Besides, as shown in FIG. 6A, the cutting unit 63 further comprises a second flexible element 635 locating between the first connecting component 632 and the second connecting component 634. Hence, after an applied strength ceases, the second flexible element 635 may provide a returning force enabling the first connecting component 632 and the second connecting component 634 to return to the original position (i.e., before the application of the strength). Herein, the second flexible element 635 is a leaf spring.

Figure 6B:
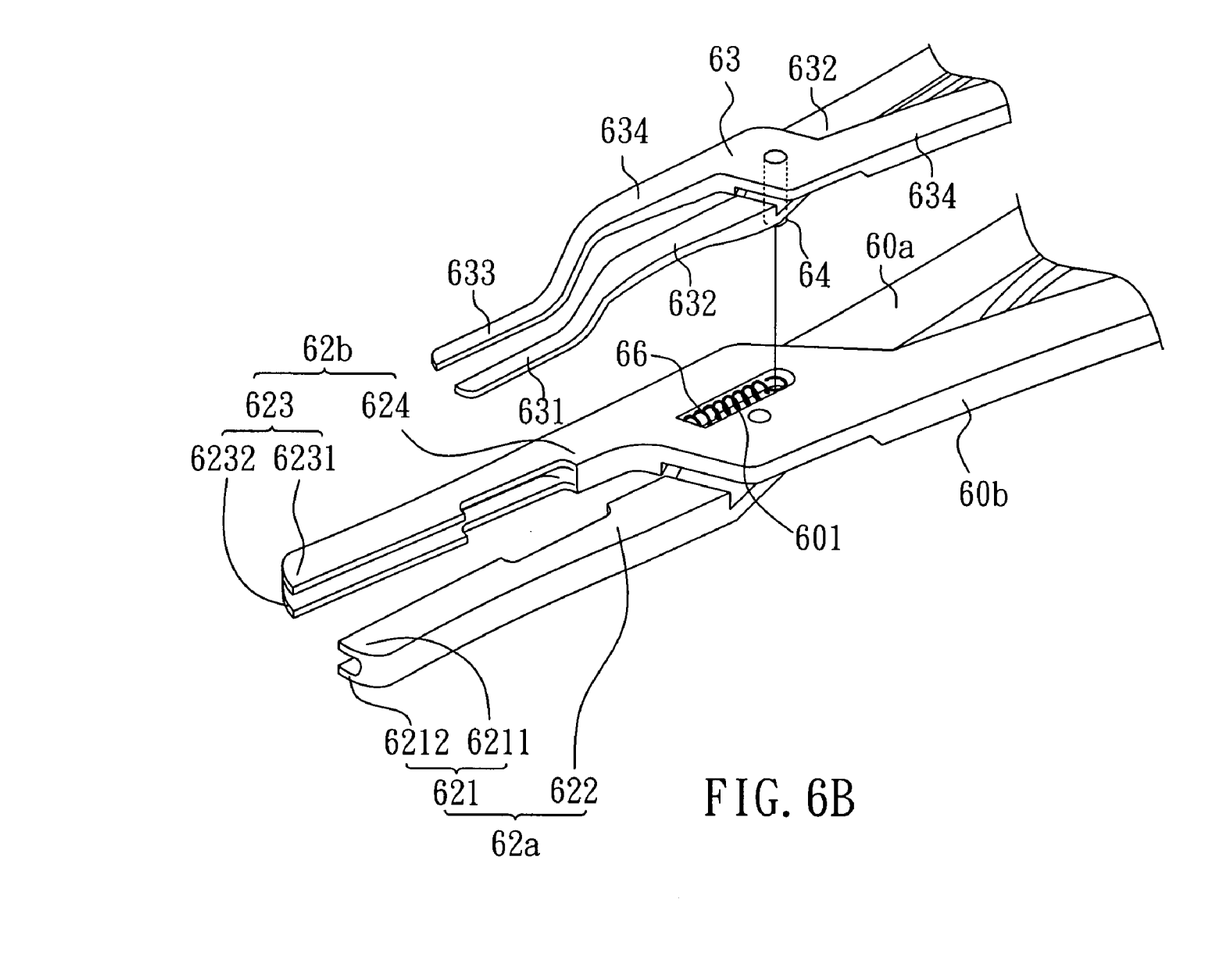
FIG. 6B is a schematic view of one part of the clip applier for clamping ligating clips of still another preferred example of the present invention.

Referring with FIG. 6B, the second clip unit 60b has a groove 601 for receiving the advancing unit 64 and enabling the advancing unit 64 to move in the groove, the advancing unit 64 connects with the first connecting component 632 and the second connecting component 634 to enable the cutting unit 63 to be pushed toward the first end 621 of the first jaw unit 62a and the second end 623 of the second jaw unit 62b by the advancing unit 64. Also, as shown in FIG. 6B, an elastic element 66 is received in the groove 601, in which one end of the elastic element 66 connects to the advancing unit 64 and the other end connects to the edge of the groove 601, and therefore the elastic element 66 may provide a returning force enabling the advancing unit 64 to return to its original position (i.e., before the application of the strength).

Therefore, the clip applier of the present example may be utilized (operated) using the same steps shown in FIGS. 3A to 3B. The two clamping positions are clamped in a single step, and then the cutting unit is moved toward the cutting position to cut/scissor the blood vessel to complete the cutting process by using the clip applier of the present example.

Example 5

Figure 7A:
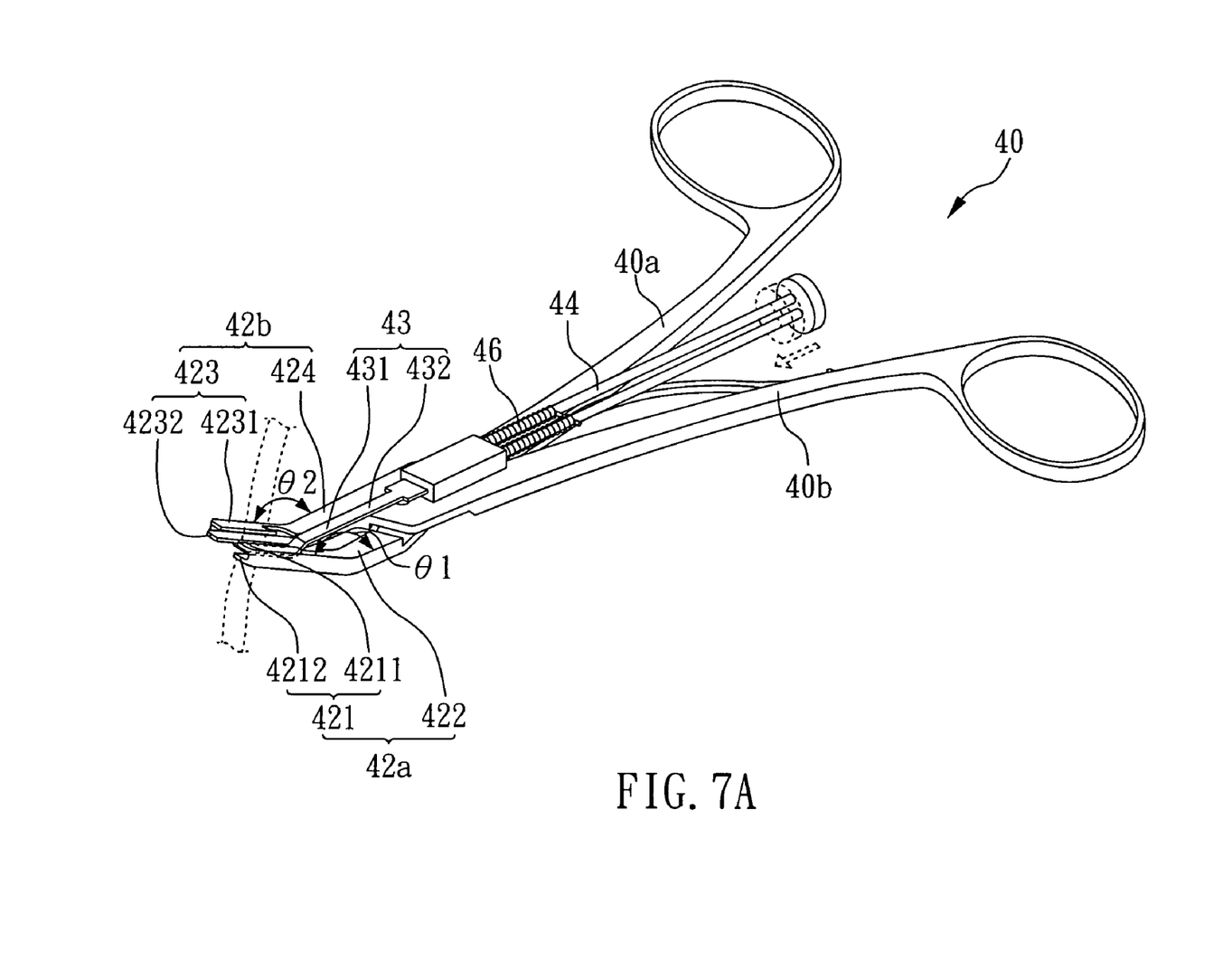
FIG. 7A is a schematic view of a clip applier for clamping ligating clips of still another preferred example of the present invention.
Figure 7B:
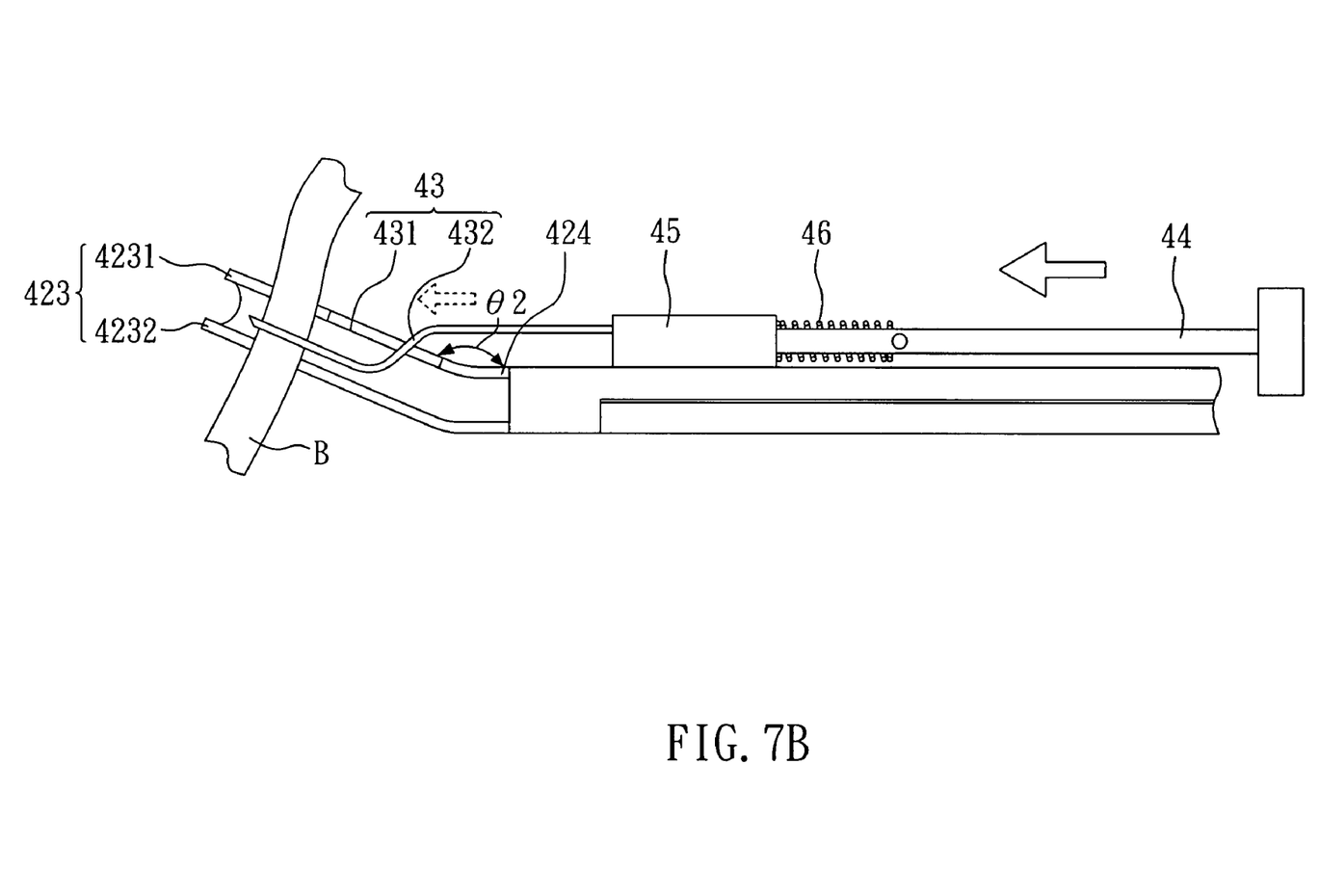
FIG. 7B is a schematic view showing a clamped blood vessel cut by the clip applier of still another preferred example of the present invention.

Referring with FIG. 7A, a clip applier 40 for clamping ligating clips of the present example is shown. Except that the first end 421 of the first jaw unit 42a connects to the first elongation part 422 with a first angle θ1, and the second end 423 of the second jaw unit 42b connects to the second elongation part 424 with a second angle θ2 (also referring with FIG. 7B), the other features and components in the present example are the same as those of example 1. Herein, the first jaw unit 42a and the second jaw unit 42b are formed in an angled shape, and the first angle θ1 and the second angle θ2 are both about 125°. However, the first angle θ1 and the second angle θ2 are not limited thereto, and may be any angle ranged from 90° to 180°.

The clip applier of the present example may be utilized (operated) with the same steps of example 1. Also referring with FIGS. 7A and 7B, the cutting unit 43 locates on the first clip unit 40a and the second clip unit 40b, and the first end 421 and the second end 423 incline from the first clip unit 40a and the second clip unit 40b. The first connecting component 432 of the cutting unit 43 is angled to enable the first cutting component 431 to locate at a position corresponding to the cutting position of the blood vessel B. Herein, the shape of the first connecting component 432, or the angle of the angled first connecting component 432 of the cutting unit 43 is determined depending on the first angle θ1 and the second angle θ2.

Example 6

Figure 8A:
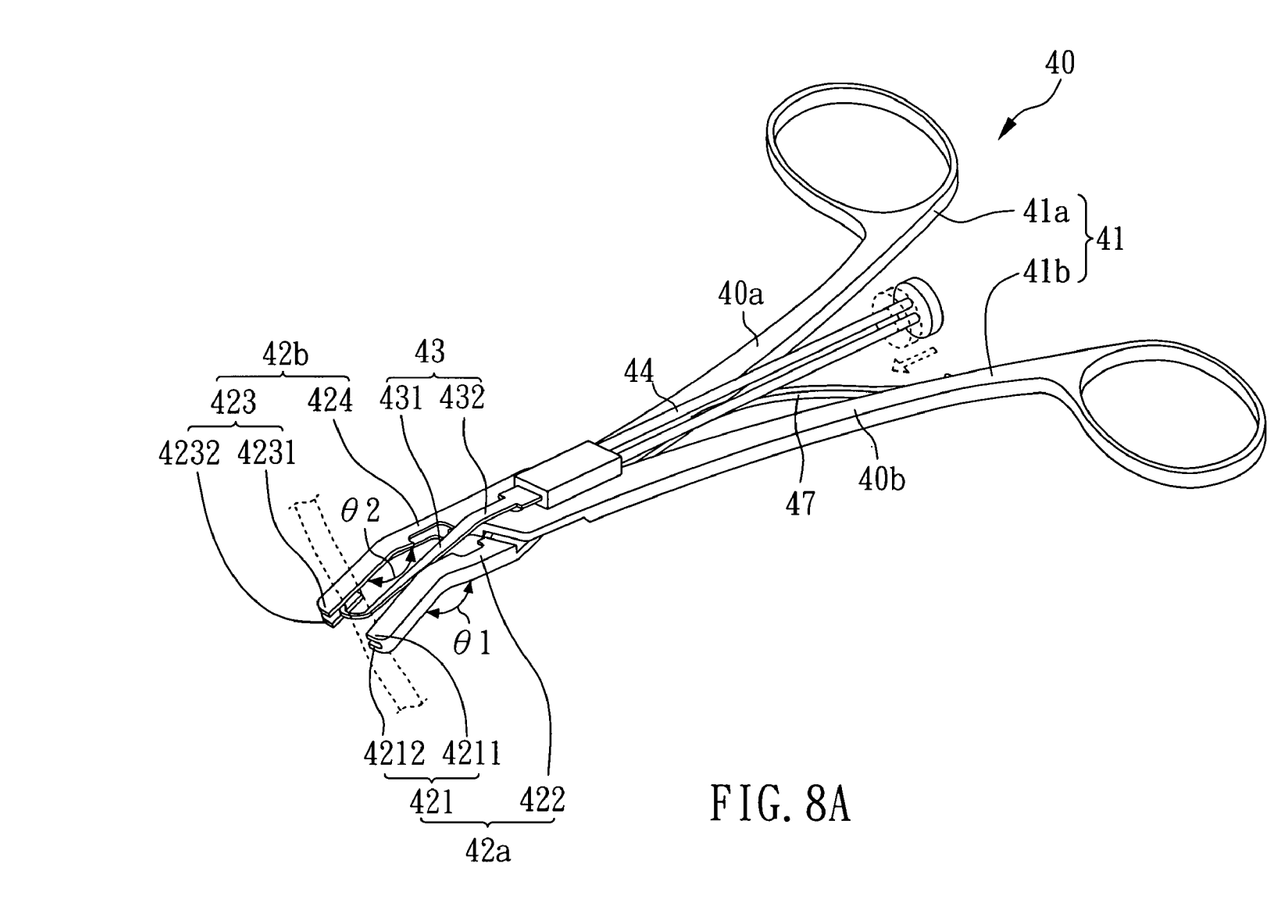
FIG. 8A is a schematic view of a clip applier for clamping ligating clips of still another preferred example of the present invention.
Figure 8B:
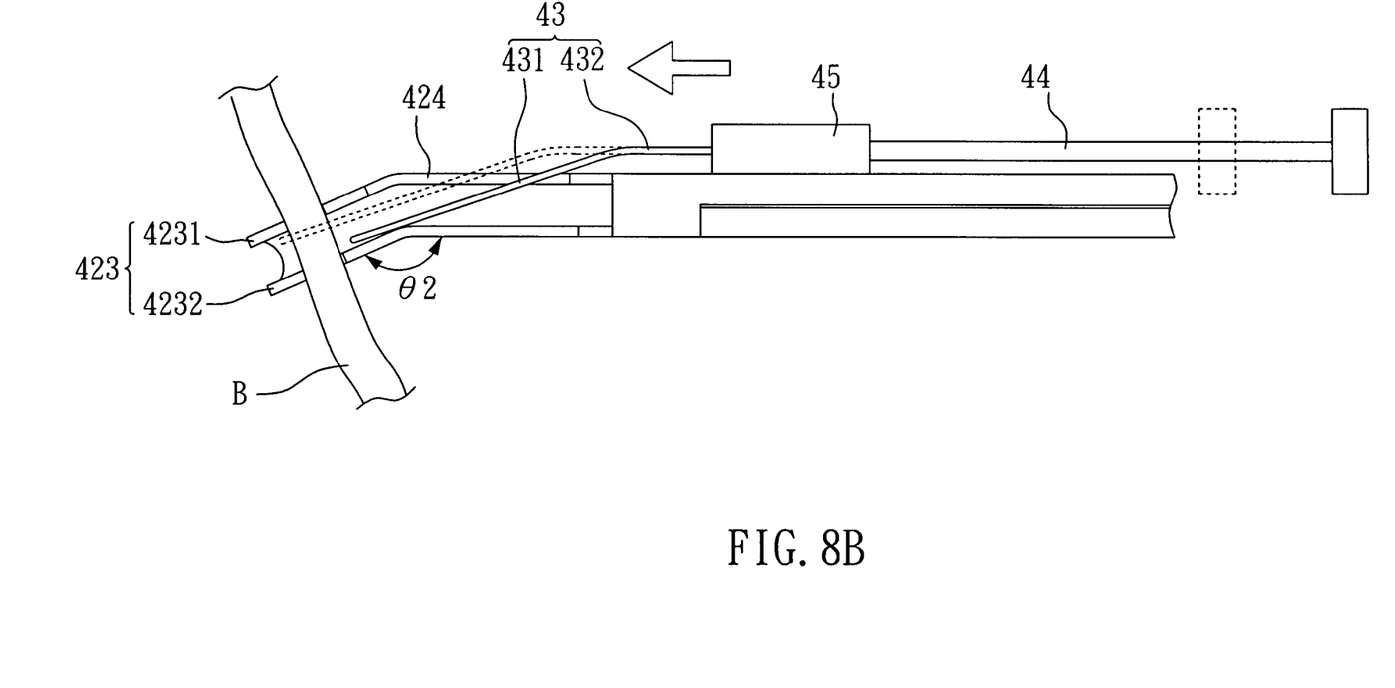
FIG. 8B is a schematic view showing the action of the clip applier of still another preferred example of the present invention.

Referring with FIG. 8A, a clip applier 40 for clamping ligating clips of the present example is shown. Except that the elastic element is eliminated in the present example; the first end 421 of the first jaw unit 42a connects to the first elongation part 422 with a first angle θ1; and the second end 423 of the second jaw unit 42b connects to the second elongation part 424 with a second angle θ2 (also referring with FIG. 8B), the other features and components of the clip applier 40 in the present example are the same as those of example 2. Herein, the first jaw unit 42a and the second jaw unit 42b are formed in an angled shape, and the first angle θ1 and the second angle θ2 are both about 125°. However, the first angle θ1 and the second angle θ2 are not limited thereto and may be any angle ranged from 90° to 180°.

The clip applier of the present example may be utilized (operated) with the same steps of example 2. Also referring with FIGS. 8A and 8B, the cutting unit 43 locates on the first clip unit 40a and the second clip unit 40b, and the first end 421 and the second end 423 are angled lowered from the first clip unit 40a and the second clip unit 40b. The first connecting component 432 of the cutting unit 43 is angled to enable the first cutting component 431 to locate at a position corresponding to the cutting position of the blood vessel B. Herein, the shape of the first connecting component 432, or the angle of the angled first connecting component 432 of the cutting unit 43 is determined depending on the first angle θ1 and the second angle θ2.

In the present example, the angled direction of the first end 421 and the second end 423 is each different from the angled directions of those in example 7, as shown in FIGS. 7A and 8A.

Alternatively, other angled directions or angles (the first angle θ1 and the second angle θ2) may be selectively used to enhance a better performance of the clip applier for the surgical usage.

Although the present invention has been explained in relation to its preferred embodiment, it is to be understood that many other possible modifications and variations can be made without departing from the scope of the invention as hereinafter claimed.

What is claimed is:

1. A clip applier for clamping ligating clips, including:
   a handle unit;
   a first jaw unit including a first end having a first upper clipping portion and a first lower clipping portion, in which a first interval exists between the first upper clipping portion and the first lower clipping portion;
   a second jaw unit including a second end having a second upper clipping portion and a second lower clipping portion, in which a second interval exists between the second upper clipping portion and the second lower clipping portion;
   an advancing unit; and
   a cutting unit, wherein the cutting unit connects to the advancing unit, the cutting unit is moved by the operation of the advancing unit, one end of the cutting unit locates in between the first jaw unit and the second jaw unit, and the advancing unit enables the cutting unit to move toward the ends of the first jaw unit and the second jaw unit;
   wherein the first upper clipping portion corresponds to the second upper clipping portion to clamp a first ligating clip by operating the handle unit, the first lower clipping portion corresponds to the second lower clipping portion to clamp a second ligating clip by operating the handle unit, such that the first ligating clip and the second ligating clip are arranged for simultaneously clamping two clamping positions of a blood vessel.

2. The clip applier for clamping ligating clips as claimed in claim 1, wherein the handle unit has a first handle and a second handle, the first jaw unit and the first handle integrally form a first clip unit, the second jaw unit and the second handle integrally form a second clip unit, and the first clip unit and the second clip unit are pivotally connected.

3. The clip applier for clamping ligating clips as claimed in claim 2, further comprising a first flexible element located between the first clip unit and the second clip unit.

4. The clip applier for clamping ligating clips as claimed in claim 3, wherein the first flexible element is a spring or a leaf spring.

5. The clip applier for clamping ligating clips as claimed in claim 2, wherein the first clip unit or the second clip unit has a groove for receiving the advancing unit and enabling the advancing unit to move in the groove.

6. The clip applier for clamping ligating clips as claimed in claim 5, further comprising an elastic element received in the groove, and one end of the elastic element connects with the advancing unit.

7. The clip applier for clamping ligating clips as claimed in claim 6, wherein the other end of the elastic element connects to the edge of the groove.

8. The clip applier for clamping ligating clips as claimed in claim 2, further comprising a fixing part locating on the first clip unit or on the second clip unit, wherein the fixing part has a channel cavity, and the advancing unit passes through the channel cavity.

9. The clip applier for clamping ligating clips as claimed in claim 1, wherein the cutting unit comprises a first cutting component and a first connecting component, the first cutting component connects with the first connecting component, and the first connecting component connects with the advancing unit.

10. The clip applier for clamping ligating clips as claimed in claim 9, wherein the cutting unit further comprises a second cutting component and a second connecting component, the second cutting component connects with the second connecting component, and the first connecting component and the second connecting component are pivotally connected.

11. The clip applier for clamping ligating clips as claimed in claim 10, wherein the cutting unit further comprises a second flexible element locating between the first connecting component and the second connecting component.

12. The clip applier for clamping ligating clips as claimed in claim 11, wherein the second flexible element is a spring or a leaf spring.

13. The clip applier for clamping ligating clips as claimed in claim 1, wherein the cutting component is a blade or a billhook.

14. The clip applier for clamping ligating clips as claimed in claim 1, further comprising an elastic element wrapping around the advancing unit, wherein one end of the elastic element connects with the advancing unit.

15. The clip applier for clamping ligating clips as claimed in claim 14, wherein the other end of the elastic element connects with the fixing part.

16. The clip applier for clamping ligating clips as claimed in claim 1, wherein the first jaw unit further comprises a first elongation part, the second jaw unit further comprises a second elongation part, the first elongation part connects to the first end, and the second elongation part connects to the second end.

17. The clip applier for clamping ligating clips as claimed in claim 16, wherein the first elongation part connects to the first end with a first angle, and the second elongation part connects to the second end with a second angle.

18. The clip applier for clamping ligating clips as claimed in claim 17, wherein the first angle is ranged from 90 to 180 degrees.

19. The clip applier for clamping ligating clips as claimed in claim 17, wherein the second angle is ranged from 90 to 180 degrees.

20. The clip applier for clamping ligating clips as claimed in claim 17, wherein the first angle and the second angle are the same.

* * * * *